(12) United States Patent
Ozin et al.

(10) Patent No.: US 9,213,000 B2
(45) Date of Patent: Dec. 15, 2015

(54) PHOTONIC CRYSTAL COMBINATORIAL SENSOR

(75) Inventors: Geoffrey A. Ozin, Toronto (CA); Leonardo da Silva Bonifacio, Toronto (CA)

(73) Assignee: OPALUX, INCORPORATED, Toronto (CA)

( * ) Notice: Subject to any disclaimer, the term of this patent is extended or adjusted under 35 U.S.C. 154(b) by 594 days.

(21) Appl. No.: 13/502,310
(22) PCT Filed: Oct. 6, 2010
(86) PCT No.: PCT/CA2010/001604
§ 371 (c)(1), (2), (4) Date: Aug. 1, 2012
(87) PCT Pub. No.: WO2011/044682
PCT Pub. Date: Apr. 21, 2011

(65) Prior Publication Data
US 2012/0293802 A1 Nov. 22, 2012

Related U.S. Application Data

(60) Provisional application No. 61/252,489, filed on Oct. 16, 2009.

(51) Int. Cl.
*G01N 21/00* (2006.01)
*G01N 21/77* (2006.01)
(Continued)

(52) U.S. Cl.
CPC ............. *G01N 21/7703* (2013.01); *G01D 5/28* (2013.01); *G01N 21/45* (2013.01); *G01N 21/78* (2013.01);
(Continued)

(58) Field of Classification Search
CPC ............ G01N 21/7743; G01N 33/54373; G01N 21/648; G01N 21/253; G01N 21/6428; G01N 21/7746; G01N 21/658; G01N 2021/7776; G01N 21/4788; G01N 21/552; G01N 2021/7773; G01N 2021/7786; G01N 2021/7789
See application file for complete search history.

(56) References Cited

U.S. PATENT DOCUMENTS

| | | | |
|---|---|---|---|
| 7,436,596 B2 * | 10/2008 | Robertson | .................... 359/587 |
| 7,489,846 B2 | 2/2009 | Grot et al. | |
| 2006/0147169 A1 | 7/2006 | Sugita et al. | |
| 2008/0212102 A1 | 9/2008 | Nuzzo et al. | |

(Continued)

FOREIGN PATENT DOCUMENTS

| | | |
|---|---|---|
| JP | 2008 232925 | 10/2008 |
| WO | WO 2007/008440 A2 | 1/2007 |

OTHER PUBLICATIONS

European Extended Search Report issued in European Patent Application 10822952.7, dated Apr. 9, 2013.
(Continued)

*Primary Examiner* — Michael P Stafira
(74) *Attorney, Agent, or Firm* — Norton Rose Fulbright US LLP

(57) ABSTRACT

The present disclosure provides methods, systems and devices for a photonic crystal combinatorial sensor. The photonic crystal sensor may include an array of photonic crystal materials, wherein each photonic crystal material has a reflected wavelength in a respective initial wavelength range. At least one a first one of the photonic crystal materials may be configured to have a response to an external stimulus different from at least a second one of the photonic crystal materials, the different response resulting in a change in the reflected wavelength of the first photonic crystal material that is an optically detectable difference from the second photonic crystal material. The optically detectable difference may provide an optically detectable response pattern of reflected wavelengths in the array. The sensor may be reversible and reusable.

27 Claims, 12 Drawing Sheets

(51) Int. Cl.
  *G01D 5/28* (2006.01)
  *G01N 21/78* (2006.01)
  *G01N 21/45* (2006.01)
  *G01N 21/21* (2006.01)
  *G02B 6/122* (2006.01)

(52) U.S. Cl.
  CPC .. *G01N 2021/213* (2013.01); *G01N 2021/7773* (2013.01); *G01N 2021/7776* (2013.01); *G02B 6/1225* (2013.01)

(56) References Cited

U.S. PATENT DOCUMENTS

2008/0278722 A1  11/2008  Cunningham et al. ........ 356/317
2009/0111169 A1   4/2009  Kim et al. .................. 435/287.1

OTHER PUBLICATIONS

International Search Report for PCT/CA2010/001604 dated Feb. 1, 2011.
Written Opinion for PCT/CA2010/001604 dated Dec. 6, 2010.

* cited by examiner

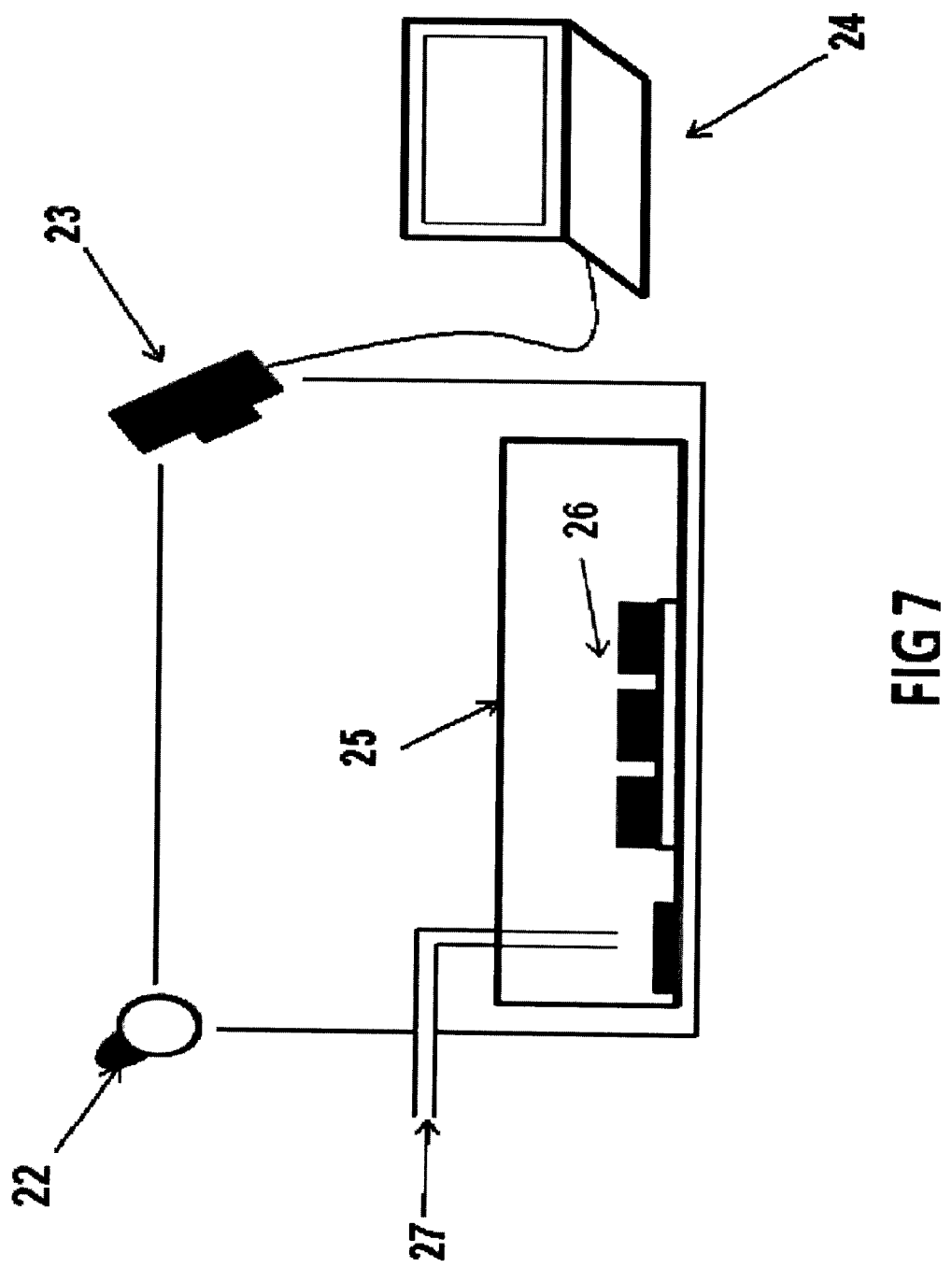

PHOTONIC CRYSTAL COMBINATORIAL SENSOR

CROSS-REFERENCE TO RELATED APPLICATIONS

This application claims the priority benefit of Ozin, International Application Serial No. PCT/CA2010/001604, filed on Oct. 6, 2010, entitled "PHOTONIC CRYSTAL COMBINATORIAL SENSOR" which claims the priority benefit of U.S. Provisional Patent Application No. 61/252,489, filed Oct. 16, 2009, entitled "PHOTONIC CRYSTAL COMBINATORIAL SENSOR" the contents of which are expressly incorporated herein by reference in their entirety, including any references therein.

FIELD OF TECHNOLOGY

The present disclosure is related to devices, methods, systems and/or materials in the field of photonic crystal sensors. In particular, the present disclosure is related to devices, methods, systems and/or materials suitable for a photonic crystal combinatorial sensor.

BACKGROUND

The human or animal olfactory system may be useful its ability to identify airborne molecules using a combinatorial response, in which a library of activated olfactory receptor-neurons provides a distinguishable pattern or "fingerprint" for each type of odorant (e.g., as described in Malnic et al. (1999) Cell 96: 713; M. Zarzo (2007) Biol. Rev. 82:455). Devices and systems that mimic the olfactory system, which may be referred to as "artificial noses", may be useful for identification of vapor phase compounds. Conventional artificial noses for the detection of gas phase molecules may be based on modulation of electrical and/or gravimetric properties.

Although conventional optical sensing materials have been studied, incorporation of such materials into artificial noses may have been rare. Specific examples of such devices may include the use of conductive polymers and/or polymer composites.

Artificial nose devices based on the modulation of optical signals have been studied. For example, Dickinson et al. (Nature (1996) 382:697) describes using a fluorescence-based approach with a fiber optics array; Dickinson et al. ((1999) Anal Chem 71:2192) describes using self-encoded bead assisted detection; and Bowden et al. ((2005) Anal Chem 77:5583) describes the use of such a device for atto-molar DNA detection. Another example study, by Rakow and Suslick (Nature (2000) 406:710) describes an artificial nose based on a colorimetric approach by using an array of metal porphyrins, in which each type of porphyrin may have shown a different coordination constant with the vapor analytes, and/or may have been thought to lead to unique colour change patterns upon binding of vapor phase ligands or solvatochromic induced effects. In another example, Janzen et al. ((2006) Anal. Chem. 78:3591) describes the incorporation of a larger variety of sensing species for discrimination of 100 volatile organic compounds.

SUMMARY

In some example aspects, the present disclosure may provide a photonic crystal combinatorial sensor comprising: an array of photonic crystal materials, wherein, for each photonic crystal material, a periodic difference in refractive indices within the photonic crystal material gives rise to a reflected wavelength in a respective initial wavelength range for that photonic crystal material; wherein at least a first one of the photonic crystal materials is configured to have a response to an external stimulus different from at least a second one of the photonic crystal materials, the different response resulting in a change in the reflected wavelength of the first photonic crystal material that is an optically detectable difference from the second photonic crystal material; and wherein the optically detectable difference provides an optically detectable response pattern of reflected wavelengths in the array.

In some examples, the sensor may include one or more photonic crystal materials having one-, two- and/or three-dimensional periodic differences in refractive indices.

In some examples, the array may include a pixelated arrangement of the different photonic crystal materials.

In some examples, the photonic crystal material may have a structural response, which may be one or more of: a change in an effective refractive index of the first photonic crystal material, a change in a dimension of the first photonic crystal material, a change in a porosity of the first photonic crystal material, an infiltration of one or more pores of the first photonic crystal material, and combinations thereof.

In some examples, the sensor may be reversible back to the initial wavelength range for each photonic crystal material.

In some example aspects, the present disclosure may provide a method for optically detecting an analyte using a photonic crystal sensor, the method comprising: providing the photonic crystal combinatorial sensor described above; exposing at least a portion of the array of photonic crystal materials to the external stimulus including the analyte; optically detecting a change in the array from an initial pattern of reflected wavelengths to a second pattern of reflected wavelengths, the second pattern being indicative of the analyte; and determining presence of the analyte based on analysis of the detected change.

In some example aspects, the present disclosure may provide a use of the photonic crystal combinatorial sensor described above for detection of at least one of: a pollutant, a bacteria, a disease marker, a target chemical, a biological agent, a level of humidity, a level of concentration of an analyte, and combinations thereof.

BRIEF DESCRIPTION OF THE DRAWINGS

The present disclosure will be described with reference to the figures, in which:

FIG. 7 illustrates an example setup for detecting optical changes of an example photonic crystal combinatorial sensor;

DETAILED DESCRIPTION OF PREFERRED EMBODIMENTS OF THE INVENTION

Figure 1:
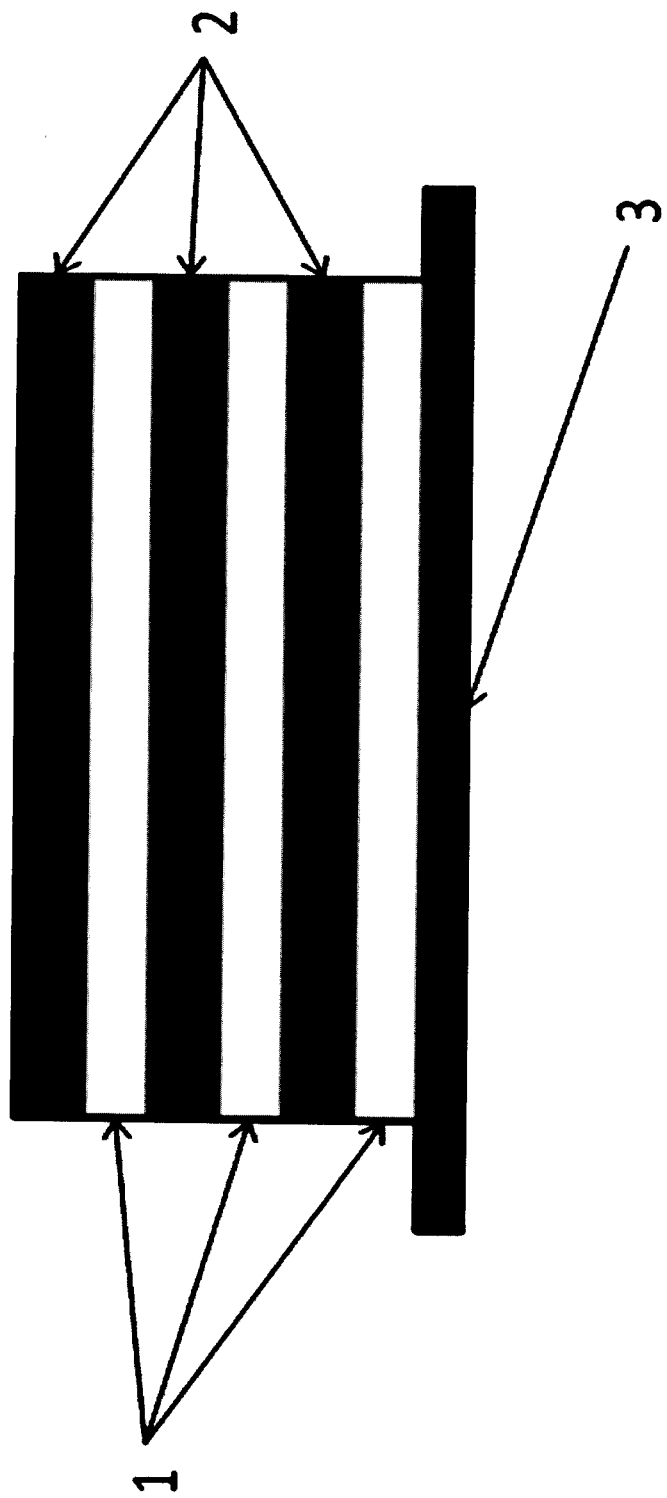
FIG. 1 is a cross-sectional representation of an example photonic crystal material.

The present disclosure provides examples of materials, methods, systems and/or devices related to photonic crystal combinatorial sensors. Such a photonic crystal sensor may also be referred to as a "photonic nose." An example photonic crystal sensor of the present disclosure may have a response to an external stimulus, which may change one or more optical properties of the sensor (e.g., a structural response resulting in a change in a structural change of a material in the sensor), resulting in a change in the reflected wavelength(s) of the sensor, in order to detect an analyte.

Conventional artificial nose devices or sensor devices typically do not use modulation of optical properties (e.g., based on a structural response of the sensor, such as a change in the refractive index or a change in a physical dimension) for detecting an analyte.

In some examples, the photonic crystal sensor may be based on an array of photonic crystal materials (e.g., in a two-dimensional pixelated arrangement). Each photonic crystal material in the array may be referred to as a "pixel", although it should be understood that such pixels may be different in size and/or shape, may be in close-packed or spaced-apart arrangement, and/or may be regularly or irregularly arranged. Each photonic crystal material may have a periodic difference in refractive indices, such as a one-, two- or three-dimensional periodic difference, which may give rise to an initial reflected wavelength for that material. The periodic difference in refractive index of a given photonic crystal material in the array may arise due to a periodic difference in the constituents (e.g., different constituents with different refractive indices) and/or the structure (e.g., porosity) of the photonic crystal material.

For example, one or more of the photonic crystal materials may include alternating layers of a first constituent and a second constituent, the alternating layers having a one-dimensional periodic difference in refractive indices. For example, one or more of the photonic crystal materials may be porous one-dimensional photonic crystals and/or Bragg stacks. Where the photonic crystal material has a periodic layered structure (e.g., as in a Bragg stack), for example with period thicknesses of substantially the same order as the wavelength of visible light, the phenomenon of Bragg diffraction may give rise to reflected light with peak wavelengths (which may also be referred to as reflectivity peaks) in the visible spectrum, which may be visually observed (e.g., by the naked human eye). Such reflected light may be visually intense, for example due to constructive interference of reflected light. The array of photonic crystal materials may include a combination of materials having different dimensions of periodicity.

In the array, at least two of the photonic crystal materials may be configured to have different responses to an external stimulus (e.g., different degree or intensity of response, different type of response, presence or absence of any response). For example, the photonic crystal materials may exhibit a structural response. A structural response may mean a change in the effective refractive index (e.g., as explained below) of the material, for example due to changes in the structure of the material (e.g., changes in porosity and/or a physical dimension, such as a layer thickness) and/or infiltration or removal of compounds into or from the material. The different responses may result in an optically detectable (e.g., visually detectable by the naked human eye) difference in changes of the respective reflected wavelengths. For example, one pixel may exhibit a wavelength shift in the reflected wavelength when exposed to a certain external stimulus (e.g., a test sample) while another pixel (a different photonic crystal material) may exhibit a different amount of wavelength shift, a different direction of wavelength shift, or no shift in the reflected wavelength. Such difference(s) may be optically detectable, for example visually by the naked human eye and/or using optical sensors (e.g., charge-coupled devices) This optically detectable difference may provide an optically detectable response pattern (e.g., detectable by the naked human eye and/or using optical sensors) of reflected wavelengths in the array, that may be indicative of the external stimulus (e.g., an optical "signature").

That is, the difference in optical response (e.g., difference(s) in wavelength shift of a Bragg diffraction/reflection spectrum of the pixels) may provide a combinatorial optical pattern (e.g., a color pattern), that may be optically distinguishable and may be used for identification and/or discrimination of one or more analytes (e.g., chemical compounds/molecules, biological compounds/molecules, and/or microorganisms) within a test sample. The analyte(s) and/or the test sample may be provided as a solid, liquid and/or gas.

In the present disclosure, it should be understood that "optics" or "optical" may be used to refer to light in all wavelengths, not just the visible wavelengths.

In some examples, the reflected wavelength of the aforementioned photonic crystal materials may arise at least partially due to their structure (which may also be referred to as "structural color") rather than from absorption and/or fluorescence of species (e.g., dyes, pigments, chromophores and/or nanocrystals) as may be the case in conventional optical sensors and artificial noses.

Example features of the reflectance spectrum of the photonic crystal material, such as reflectivity, peak wavelength and/or bandwidth, may be related to the refractive index and/or thicknesses of each layer of the photonic crystal material. For example, by using one or more porous constituents for one or more layers of the photonic crystal material, it may be possible to dynamically manipulate the refractive index of the layer(s) by controlling what may be referred to as an "effective refractive index". The effective refractive index may be determined from a weighted average of the actual refractive index of the constituent(s) and of the composition of what is in the pores of the material. For example, the effective refractive index may be changed by replacement of a medium in the pores, such as air (having refractive index=1.00), by an analyte (e.g., having refractive index >1.0). This change in the effective refractive index may result in a red-shift of the reflected wavelength peak where the effective refractive index of the layer(s) is increased, or a blue-shift of the reflected wavelength peak where the effective refractive index of the layer(s) is decreased. Such wavelength shift may be optically detectable, for example this may be visually observed (e.g., by the naked human eye) as a detectable change in color.

In some examples, exposure of such porous Bragg stacks to one or more analytes may lead to surface adsorption (e.g., through chemical and/or physical binding) depending on the nature of the analyte(s), which may result in an increase or decrease in the effective refractive index and/or a concomitant change in the reflected wavelength. In some examples, alternative or in addition to a change in the effective refractive index, one or more photonic crystal materials possessing swelling and shrinking capabilities may also be used, in which the material may respond to an external stimulus (e.g., an analyte) through a change in the thickness of at least one layer, and an optically detectable shift in the reflected wavelength may result.

In some examples, the photonic crystal combinatorial sensor may include an array of photonic crystal materials, which may be spatially spaced (e.g., laterally spaced). The array may include at least two photonic crystal materials with different surface features and/or functionalities that may enable each material to respond different to the exposure of a given analyte. The adsorption characteristics of each photonic crystal material may be controlled by the surface chemistry anchoring mechanisms of the constituents of the pore walls of the material. For example, the surface chemistry of a given photonic crystal material may include one or more molecules which introduce entities that may be able to modify the surface energy properties of the pores of the photonic crystal material. For example, such entities may be exemplified by, but need not necessarily be limited to, chemical groups that may modify pore chemical functionality, hydrophobicity, coulombic interactions, Van der Walls interactions, hydrogen bonding ability, Lewis and Bronsted-Lowry acid-base interactions, charge transfer complexes, dipole-dipole interactions, magnetism, and/or nanostrucural features such as molecular imprints.

In some examples, when a photonic crystal combinatorial sensor having a pixelated array of photonic crystal materials (e.g., in which each pixel has distinct surface functionality(ies)) is exposed to an external stimulus (e.g., an analyte), at least two pixels (or in some examples, each pixel) may respond differently (including, for example, difference in type of response, difference in degree of response, or difference in presence of response), for example depending on the type of interactions (e.g., intermolecular interactions) experienced by the stimulus with the pore surfaces of the pixels. The combination of the responses from all pixels in the array may be detectably different for different analytes and/or set of analytes (e.g., defining an atmosphere or environment), which may enable the discrimination of analytes and/or the compositions of different environments. Detection of the response pattern may be performed by, for example, imaging the optical change of the entire array of the sensor (e.g., with charge-coupled devices such as digital cameras) and/or using optical probe measurements, such as optical spectroscopy and/or colorimetry. Such measurements may be compared to a known initial optical pattern of the array (e.g., a reference measurement before exposure to any external stimulus). The technologies, methods, systems and/or devices described herein may be useful for detection of chemical and/or biological components of a test sample.

In some examples, the test sample may include a chemical and/or biological compound of human, animal and/or environmental origin, and may be a solid, liquid and/or gas.

For example, an application of the present disclosure may be the detection of chemical and/or biological threats for human, animal and/or vegetable species. Another example application of the present disclosure may be in human, veterinary and/or environmental diagnostics. For example, a test sample may be analyzed using the disclosed methods and devices to determine a specific chemical and/or biological signature of the test sample. For example, such a determined signature may be analyzed (e.g., through an algorithm) in order to identify a specific disease, biological threat, and/or chemical and/or biological compound. Another example application of the present disclosure may be for determination of clinical and/or health conditions of a patient (including humans and/or animals).

In some examples, the disclosed photonic crystal sensor may be based on the use of a pixelated array of functional one dimensional photonic crystal materials each having multilayers of alternating refractive index (which may be also known as Bragg Stacks (BS)). Though not intending to be bound by theory, it may be that functionality may be introduced into the pixels of the sensor by the incorporation of (meso)porosity into the layered structure of one or more of the photonic crystal materials. Bragg Stacks have been studied for use in detection of analytes, and for methods of manufacture, for example in Fuertes et al. (2007) Adv. Funct. Mater. 17"1247; Colodrero et al. (2008) Langmuir 24:4430; Colodrero et al. (2008) Langmuir 24:9135; Calvo et al. (2009) Langmuir 25:2443; and Puzzo et al. (2009) J. Mater. Chem. 19:3500, the entireties of which are hereby all incorporated by reference.

In some examples, the disclosed photonic crystal combinatorial sensor may include pixels formed by photonic crystal material(s) having relatively high surface area and/or structural response upon infiltration of one or more analytes. For example, shifts in the reflected wavelengths of the pixels may be determined by reflectivity and/or transmissivity measurements, as any change in the effective refractive indexes of the photonic crystal material upon infiltration by one or more analyte may result in a shift in the position of the reflected wavelength.

In some examples, the photonic crystal sensor may operate based upon analyte-induced modulation of one or more optical properties (e.g., Bragg diffraction properties) of a pixelated array of photonic crystal materials (e.g., an array of mesoporous 1D photonic crystal materials), in which each pixel and/or set of pixels may have different surface energies and/or adsorption-binding properties enabled through selective chemical and/or mechanical functionalization.

In some examples, the photonic crystal sensor may be a relatively simple and/or low cost, environmentally friendly and/or robust sensor device. For example, the photonic crystal sensor may provide a combinatorial pixelated optical and/or colorimetric sensor platform technology that may be able to detect and/or discriminate analytes (e.g., small molecules, biological entities, and/or micro-organisms), for example using a relatively simple imaging system (e.g., a digital camera). In some examples, the photonic crystal sensor may be suitable for use (and/or in conjunction with other steps towards its use) in diverse kinds of analyte sensing.

Reference is now made to FIG. 1. FIG. 1 is an example cross-sectional representation of a one-dimensional periodic layered structure of an example photonic crystal material that may be suitable for use in an example of the presently disclosed photonic crystal sensor. Two or more such photonic crystals may be provided in the example photonic crystal sensor.

In this example, alternating layers of a first constituent 1 and a second constituent 2 (e.g., each layer having a thickness in the range of about 30 nm to about 250 nm) may be supported on a substrate 3. In selecting the first and second constituents 1, 2, it may be useful to select constituents that have a difference of refractive index values between the resulting layers. It may also be useful for at least one of the first and second constituents 1, 2 to have some degree of porosity, which may help to confer tunability (i.e., ability to shift wavelength range of the reflected wavelength) to the photonic crystal material. In this example, the substrate 3 may be any surface (e.g., a planar or curved, smooth or rough surface) on which the layers may be supported. For example, the layers may be directly deposited or otherwise formed onto the substrate 3 (e.g., using conventional deposition methods), the layers may be attached onto the substrate 3 after being formed, or the layers may be unattached but supported by the substrate 3. In some examples, the photonic crystal combinatorial sensor may not include the substrate 3, for example where the alternating layers have sufficient rigidity and/or robustness (e.g., where the total thickness of the layers is sufficiently thick).

In some examples, porosity of the photonic crystal material may range from about 0% (e.g., in dense films) to about 74% (e.g., in inverse opals) of the volume of the photonic crystal material. The porosity may be selected depending on the type of response (e.g., structure change or effective refractive index change) and/or analyte (e.g., liquid or vapour) the sensor is intended for. In some examples, for a photonic crystal sensor that is intended to have an effective refractive index change when exposed to vapour phase stimuli, the porosity of the photonic crystal material may be in the mesopore range (e.g., in the range of about 2 nm to about 25 nm), to allow for the phenomenon of capillary condensation (i.e., where vapour phase solvents may condense into liquids in the pores). In the case of capillary condensation, pores of the photonic crystal material may change from being relatively empty (i.e., filled with air) to relatively filled with liquid, which may help to increase or maximize the change in effective refractive index and hence the detectable optical response. In some examples, for a photonic crystal sensor intended for detecting molecules at the sensor surface, it may be useful for the photonic crystal materials to have a relatively high surface area, in which case relatively smaller pores (e.g., in the range of about 5 nm to about 15 nm) may be useful (e.g., within the limit at which diffusion of analytes into the layers is still possible).

Possible constituents for the photonic crystal material may include, for example, a variety of constituents such as, for example, silicon and/or metal oxide nanoparticles and/or polymers. Porosity in one or more layers may be manufactured using, for example, inter-particle spacing and/or periodically ordered micro and/or mesoporous constituents, where porosity may be produced using a template (e.g., an organic liquid crystalline template). For example, silicon dioxide nanoparticles (e.g., with diameters of about 15 nm) and/or titanium dioxide particles (e.g., with diameter of approximately 10 nm) may be suitable constituents for the alternating layers.

Figure 2:
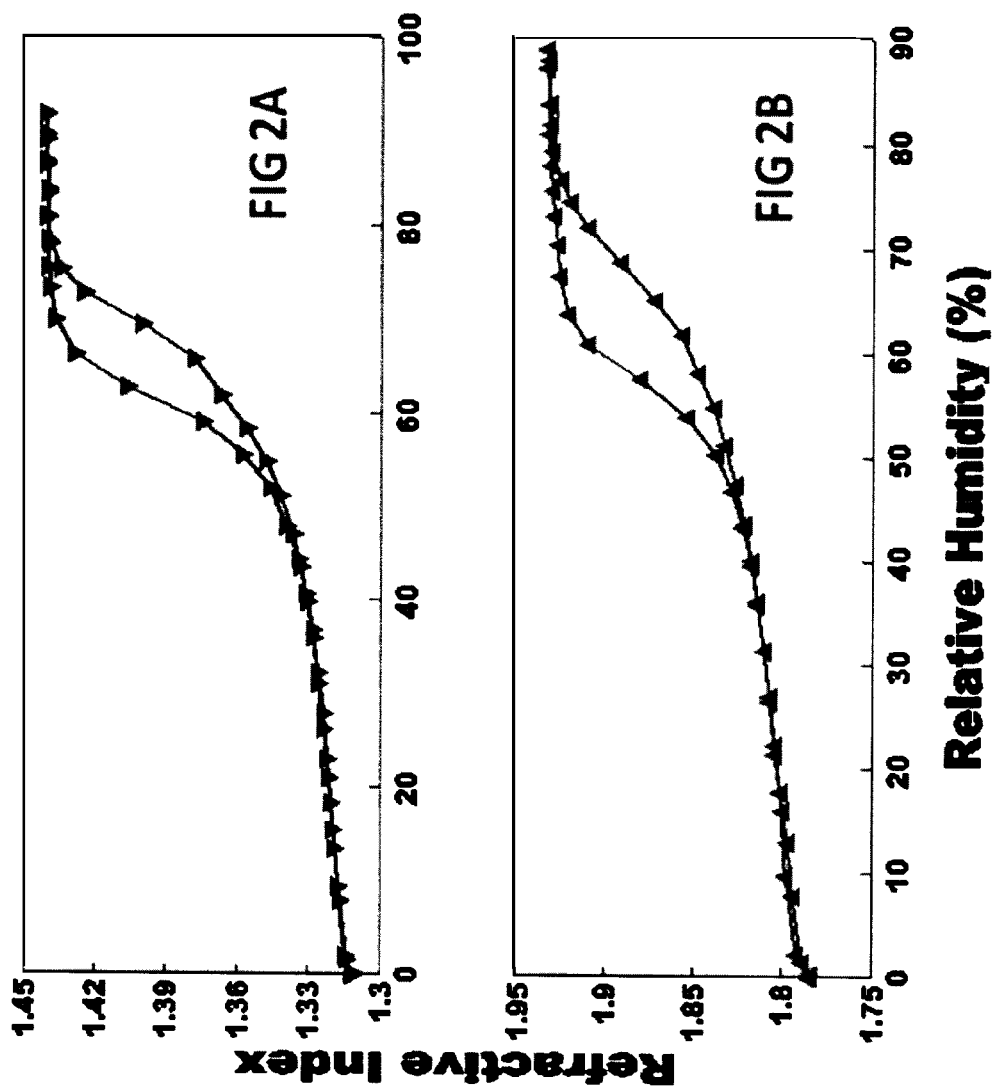
FIGS. 2A and 2B illustrate the correlation and/or dependence of the refractive index of example nanoparticle thin films with the relative humidity.

Reference is now made to FIGS. 2A and 2B. In the example of FIGS. 2A and 2B, the correlation and/or dependence of the refractive index of example thin films, which may be suitable for use in an example photonic crystal sensor, at different humidity levels are shown. In this example, the thin films are silicon dioxide nanoparticle (FIG. 2A) and titanium dioxide nanoparticle (FIG. 2B) single layered thin films, having mean nanoparticle diameters of approximately 15 nm and 10 nm, respectively, deposited on silicon wafer substrates. In this example, measurements may be carried by spectroscopic ellipsometry. This example illustrates an example of the refractive index tunability of such films. The pores of the porous thin films may be stepwisely filled (e.g., in a controlled atmosphere of water vapor), while the refractive index may be monitored (e.g., by spectroscopic ellipsometry). In this example, the films may be produced by spincoating of 30% (w/w) solutions of the respective nanoparticles on silicon wafer substrates. The example charts illustrate a relatively sharp increase in the refractive index at about 60% relative humidity, which may be due to the phenomenon of capillary condensation.

Figure 3:
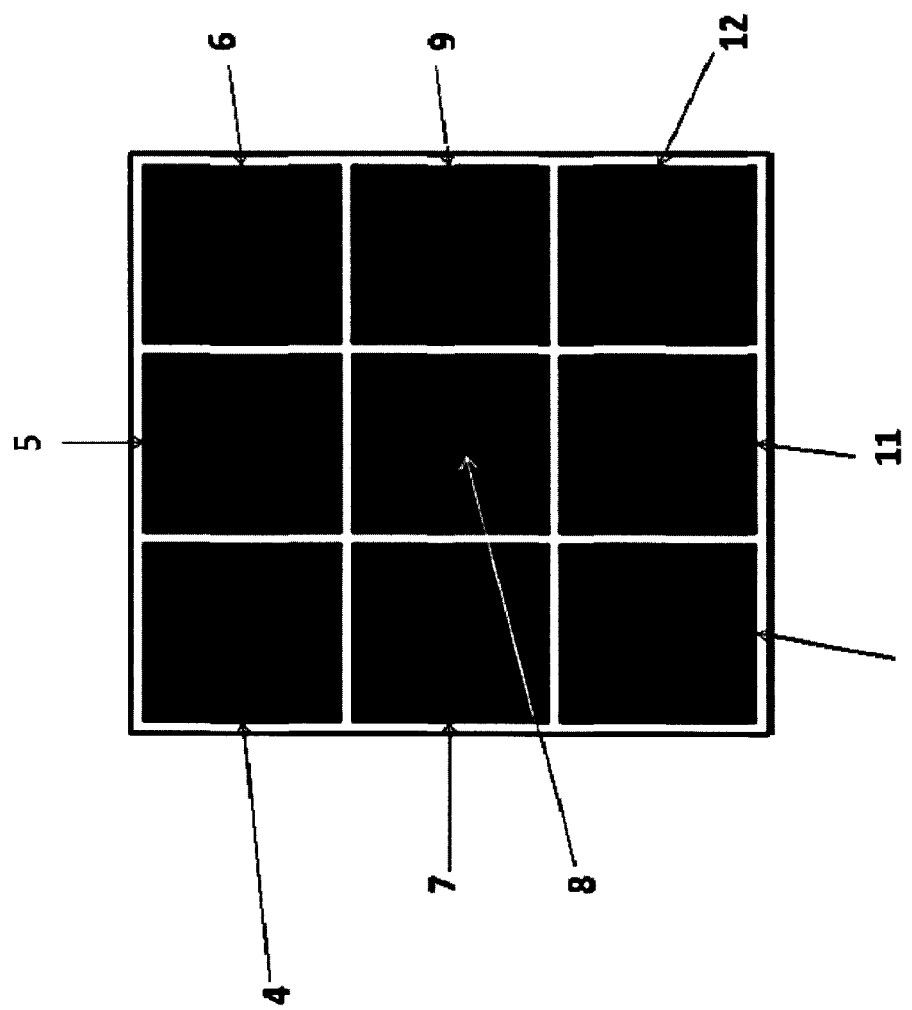
FIG. 3 illustrates an example array embodiment of a photonic crystal combinatorial sensor.

Reference is now made to FIG. 3, which illustrates an example of a photonic crystal combinatorial sensor. In this example, the photonic crystal sensor has an array of 9 photonic crystal materials ("pixels") 4-12, which may each be a Bragg stack (e.g., similar to that of FIG. 1), and each pixel may have a different surface modifications, resulting in different responses to one or more external stimuli. Although this example shows the sensor to have pixels arranged in a 3×3 array, it should be understood that other array arrangements may be suitable, including, for example, other regular or irregular arrangements, different pixel sizes and/or shapes, and/or close-packed or spaced-apart pixels.

In some examples, the photonic crystal material forming a pixel 4-12 may be formed using conventional methods. For example, the layered structure of a Bragg stack may be obtained by spin-coating one layer of the first constituent (e.g., silicon dioxide nanoparticles) and one layer of the second constituent (e.g., titanium dioxide nanoparticles), performing a calcination step (e.g., in which the film may be maintained for about 15 min at about 450° C.), and repeating the process until the desired number of layers is obtained. Such spin-coating may be performed on a suitable substrate (e.g., a silicon wafer). Other methods for manufacturing the photonic crystal material may be used including, for example, dip-coating, doctor blading, soft lithography (including, for example, micromolding, microcontact printing, microtransfer printing), dip-pen nanolithography, ink-jet printing, tiling, photolithography, wet etching, plasma etching, pen plotting, etc. Different manufacturing techniques may be used to produce different photonic crystal structures (e.g., one-, two- or three-dimensional photonic crystal materials).

To form the array of pixels shown in the example of FIG. 3, an appropriately sized piece of the fabricated photonic crystal material (e.g., obtained from a larger piece of the material) may be obtained for each pixel 4-12. Each pixel 4-12 may act as a single sensorial unit in the photonic crystal sensor. In order to obtain different responses from each pixel 4-12, each pixel 4-12 may be fabricated from different constituents and/ or with different dimensions and/or different porosity and/or different dimensionality in the periodic difference of refractive indices, alternatively or in addition each pixel 4-12 may be functionalized a different molecule, which may modify the surface properties of the photonic crystal material of each pixel 4-12, resulting in different responses to one or more external stimuli (e.g., one or more analytes).

Figure 4:
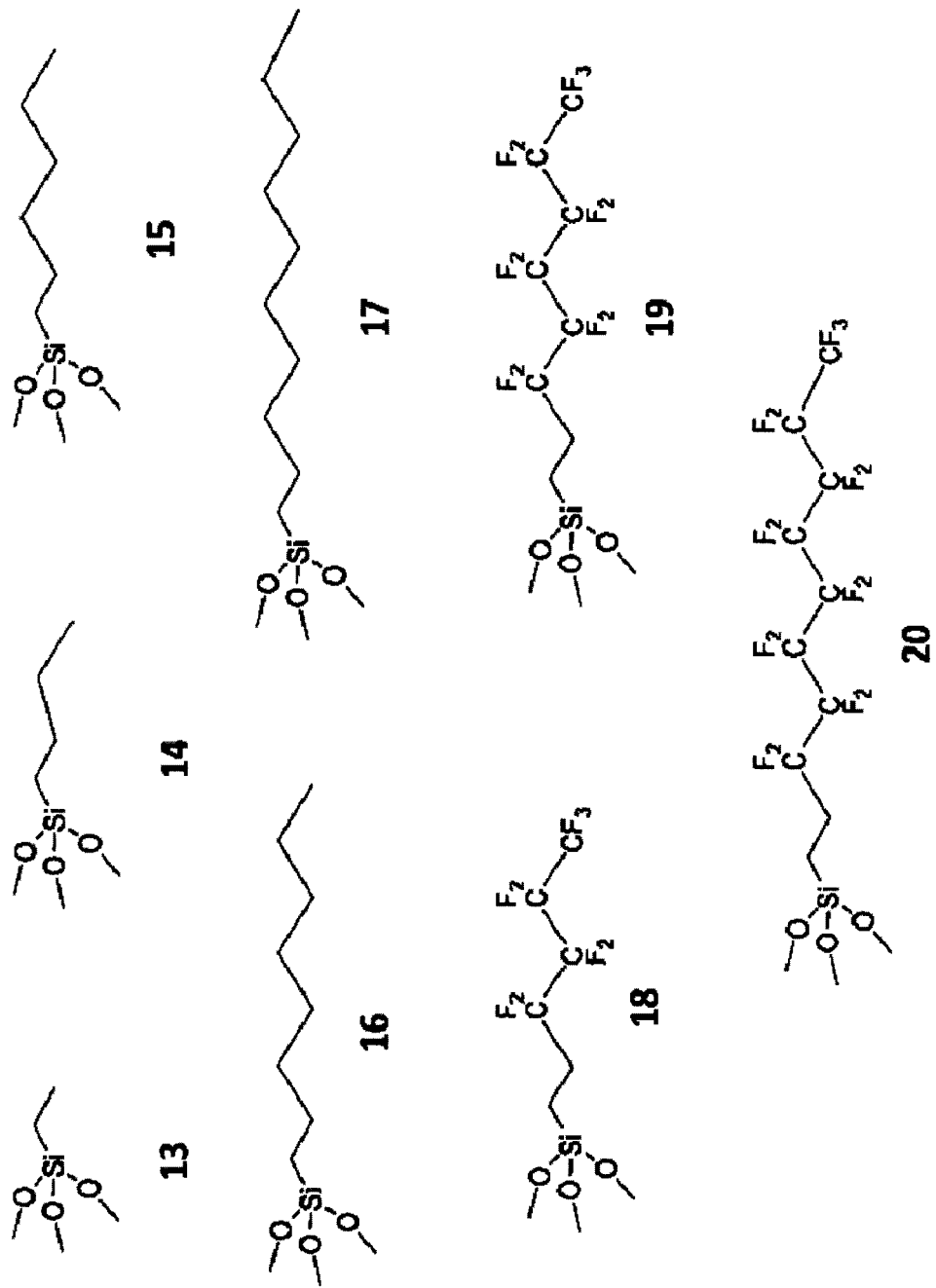
FIG. 4 shows the structures of nine molecules which may be suitable for surface functionalization reactions for an example photonic crystal combinatorial sensor.

Reference is now made to FIG. 4. FIG. 4 shows the structures of nine example molecules 13-20 which may be used for surface functionalization of the pixels 4-12. For example, pixel 4 may be not reacted with any molecule, and may be the most hydrophilic of the pixels 4-12. For example, pixel 5 may be reacted with molecule 13, pixel 6 may be reacted with molecule 14, pixel 7 may be reacted with molecule 15, pixel 8 may be reacted with molecule 16, pixel 9 may be reacted with molecule 17, pixel 10 may be reacted with molecule 18, pixel 11 may be reacted with molecule 19, and pixel 12 may be reacted with molecule 20.

Figure 5A:
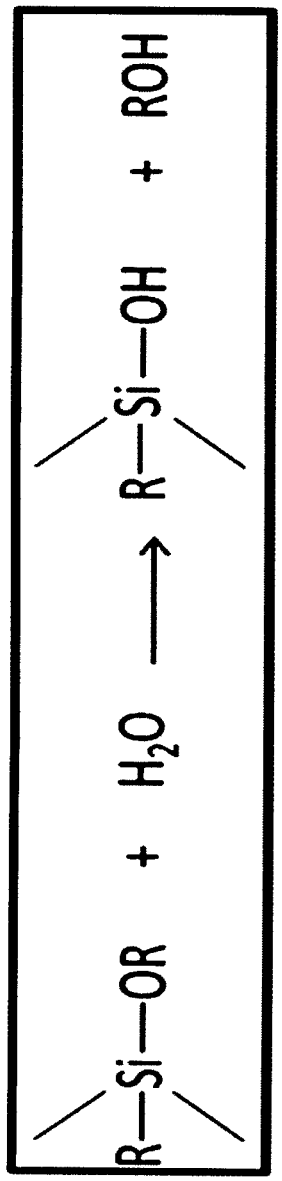
FIGS. 5A and 5B are schemes representing example reaction steps of a surface functionalization reaction for an example photonic crystal combinatorial sensor.
Figure 5B:
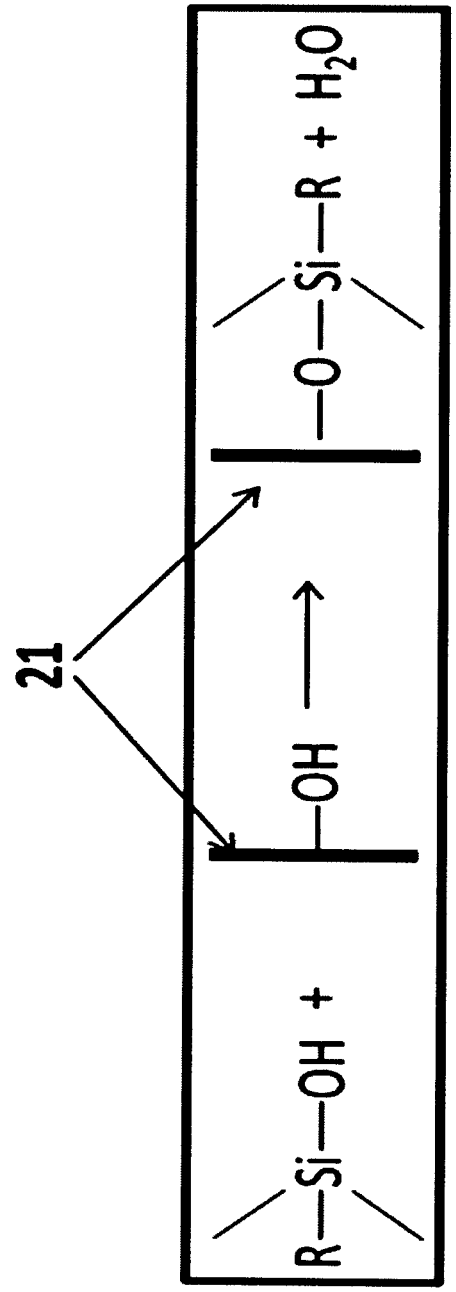

Exposure of each pixel 5-12 with solutions containing one of the molecules 13-20 may lead to example reactions involving steps represented in FIG. 5A and FIG. 5B, where a thick line 21 represents the surface of the nanoparticles in the layers of the photonic crystal material. In these example reactions, OH groups present on the surface of the layer constituents (e.g., silicon and titanium dioxide nanoparticles) may be substituted by 'R' alkyl groups, which may confer increased hydrophobicity and/or may modify the adsorption characteristic of such constituents.

Figure 6A:
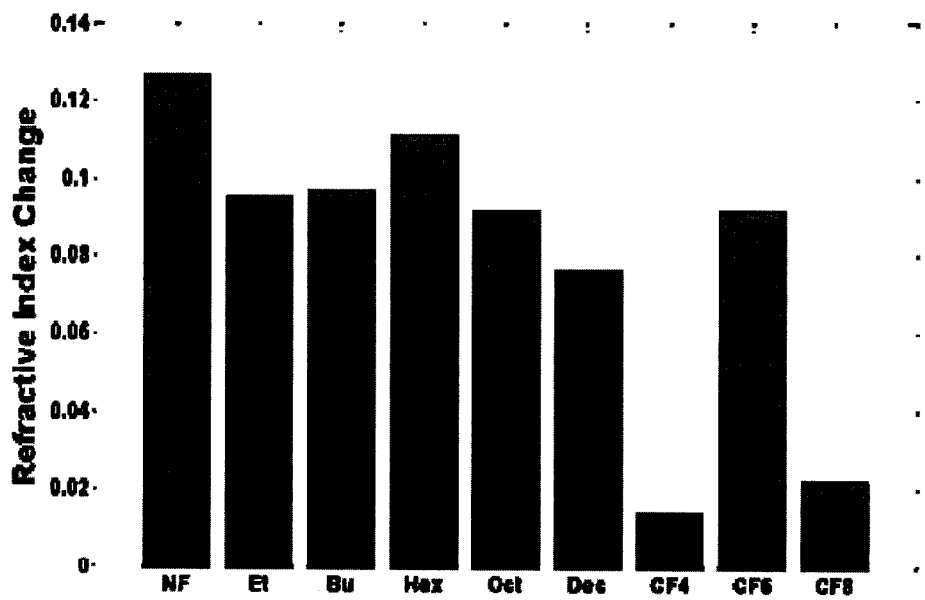
FIGS. 6A and 6B show example refractive index change measurements for different humidity levels for an example photonic crystal combinatorial sensor.
Figure 6B:
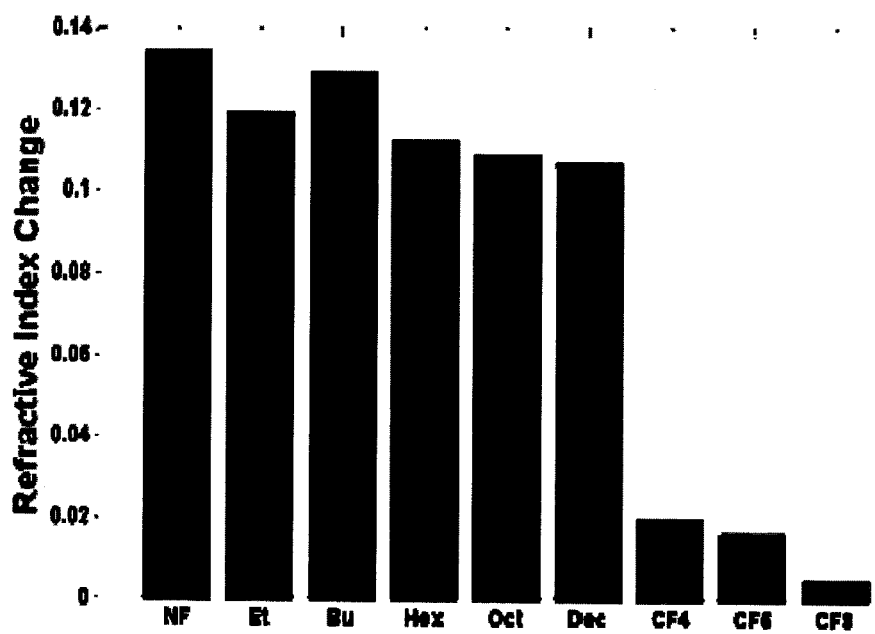

Reference is now made to FIGS. 6A and 6B. FIG. 6A and FIG. 6B show refractive index change measurements (e.g., as monitored by spectroscopic ellipsometry) for an example photonic crystal sensor when the relative humidity experienced by the sensor increases from 0% to 100% in a closed chamber. In this example, the sensor has an array of nine different photonic crystal materials, each with different surface functionalities. In this example, each photonic crystal material includes alternating layers of silicon dioxide nanoparticle thin films and titanium dioxide nanoparticle thin films. FIG. 6A shows the refractive index change measurements taken for the silicon dioxide thin films, and FIG. 6B shows the refractive index change measurements taken for the titanium dioxide thin films. In this example, each bar in the charts of FIGS. 6A and 6B corresponds to a different pixel of the photonic crystal sensor. In this example, the bar NF corresponds to a non-functionalized pixel; bar Et corresponds to a pixel functionalized with molecule 13; bar Bu corresponds to a pixel functionalized with molecule 14; bar Hex corresponds to a pixel functionalized with molecule 15; bar Oct corresponds to a pixel functionalized with molecule 16; bar Dec corresponds to a pixel functionalized with molecule 17; bar CF4 corresponds to a pixel functionalized with molecule 18; bar CF6 corresponds to a pixel functionalized with molecule 19; and bar CF8 corresponds to a pixel functionalized with molecule 20.

In some examples, the optical response pattern of the photonic crystal sensor to an external stimulus (e.g., a solvent atmosphere) may be monitored and/or determined using the example system shown in FIG. 7. In this example, an example photonic crystal combinatorial sensor 26 may be placed in a closed chamber 25 with window transparent to at least some wavelengths. The chamber 25 may include an inlet 27, for introducing an external stimulus (e.g., a solvent atmosphere) to the sensor 26. The chamber 25 may be illuminated by a light source 22 (e.g., a high color rendering index light source). The system may also include an optical detector 23 (e.g., an optical charge-coupled device (CCD) digital camera, a spectrometer, colorimeter, or an optical probe such as using multiplexed methods based on fiber optics bundles) for monitoring optical changes (e.g., color changes) of the sensor 26. In some examples, the optical detector 23 may communicate (e.g., through a wired connection or wirelessly) with a processor 24 (e.g., an external computer). The optical detector 23 may be remotely controlled using the processor 24 and the optical detector 23 may communicate raw data to the processor 24 (e.g., for storage and/or analysis).

In some examples, changes (e.g., color changes) in the optical pattern of the photonic crystal sensor may be determined by calculating the absolute difference between a reference image (e.g., a digital image of the sensor before exposure to the external stimulus) and a sample image (e.g., a digital image) obtained when or after the sensor is exposed to the external stimulus (e.g., solvent vapor). In some examples, such as where some or all of the reflected wavelengths of the photonic crystal sensor fall in the visible spectrum, the image may be acquired using the sRGB standard, so that each pixel may be represented by a triplet of color level values for the red, green and blue color channels (e.g., with each color level having a value ranging from 0 to 255). The color levels of the absolute difference image between the reference and sample images may be used to determine the response of the sensor. For example, if no color changes are observed in the sample, a triplet red=0, green=0 and blue=0 may be observed (e.g., resulting in a black absolute difference). In some examples, any color change due to the sensor's response to an external stimulus may result in a change in the color level values, resulting in a non-black absolute difference.

In some examples, after the absolute difference image is calculated, mean values of the RGB levels may be extracted from one or more selected regions of the sensor (e.g., for each of, for example, 9 pixels in the sensor), which may resulting in, for example, 27 parameters for each measurement for a sensor having 9 pixels (i.e., 3 color level values for each pixel).

In some examples, in use, the optical response of the photonic crystal sensor to a test sample may be compared to a reference (e.g., optical response to a control sample). For example, images may be obtained (e.g., at certain time intervals) of the sensor response in each case. The optical response to the test sample may then be determined by subtracting the reference response. Pattern recognition techniques (PARC) may be used to determine any differences between the test and reference responses. Example PARCs may include, for example, principle component analysis (PCA), multivariate and univariate analysis of variance, partial least square (PLS), multiple linear regression (MLR), principal component regression (PCR), discriminant function analysis (DFA) including linear discriminant analysis (LDA), and cluster analysis (CA) including nearest neighbor (NN), as well as biologically-motivated methodologies including, for example, artificial neural networks (ANNS) including multilayer perceptron (MLP), fuzzy inference systems (FIS), self-organizing map (SOM), radial basis function (RBF), genetic algorithms (GAS), neuro-fuzzy systems (NFS) and adaptive resonance theory (ART). Other methods of data analysis may also be used.

Although measurement and analysis using the disclosed photonic crystal sensor has been described as being based on the use of digital images, any other methods for optical measuring and/or analyzing may be suitable.

Figure 10:
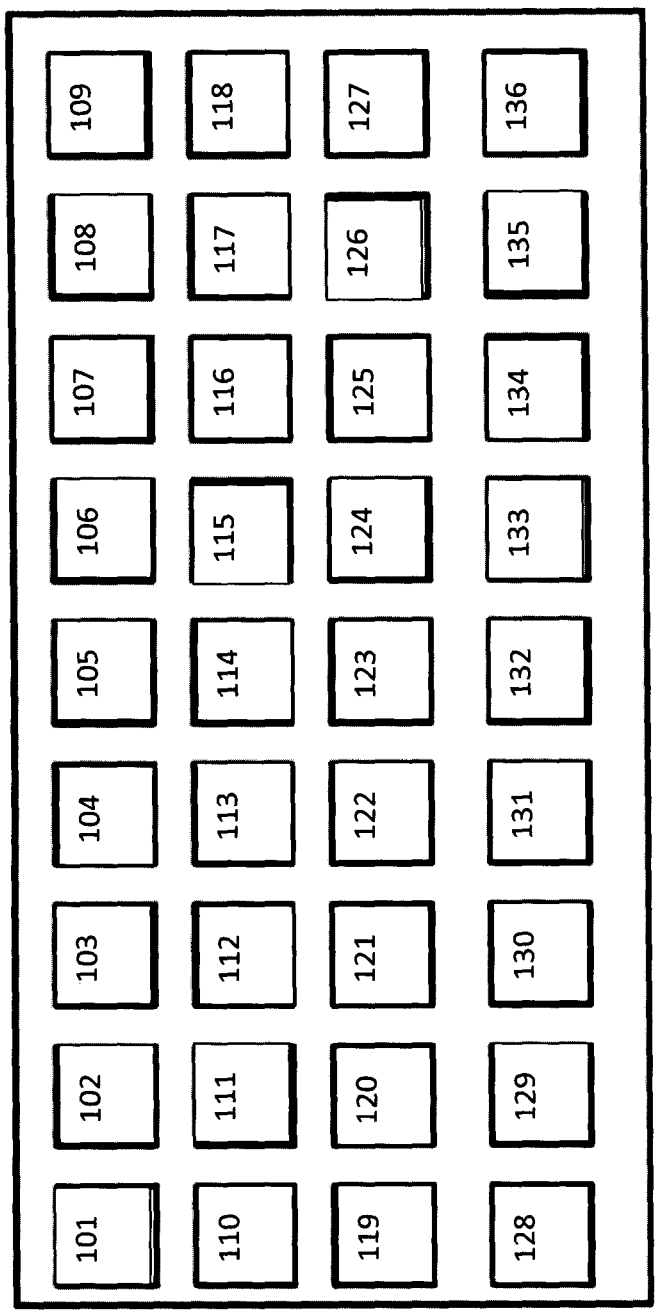
FIG. 10 shows another example photonic crystal sensor.

Reference is now made to FIG. 10. In the example of FIG. 10, an example photonic crystal combinatorial sensor may include an array with larger number of different photonic crystal materials. In this example, the photonic crystal sensor may have 36 pixels 101-136. In this example, the different pixels 101-136 may have different surface functionalization with the following example molecules:

| Pixel number | Surface functionalization molecule |
|---|---|
| 1 | METHYLTRIETHOXYSILANE |
| 2 | ETHYLTRIETHOXYSILANE |
| 3 | n-PROPYLTRIETHOXYSILANE |
| 4 | HEXYLTRIMETHOXYSILANE |
| 5 | n-OCTYLTRIETHOXYSILANE |
| 6 | DODECYLTRIETHOXYSILANE |
| 7 | HEXYLTRIMETHOXYSILANE |
| 8 | n-OCTADECYLTRIETHOXYSILANE |
| 9 | PHENETHYLTRIMETHOXYSILANE |
| 10 | 3-AMINOPROPYLTRIETHOXYSILANE |
| 11 | N-(TRIMETHOXYSILYLPROPYL)ISOTHIO-URONIUM CHLORIDE |
| 12 | (3-TRIMETHOXYSILYLPROPYL)DIETHYLENETRIAMINE |
| 13 | UREIDOPROPYLTRIETHOXYSILANE |
| 14 | N•TRIMETHOXYSILYLPROPYL-N,N,N-TRIMETHYL-AMMONIUM CHLORIDE |
| 15 | 2-CYANOETHYLTRIETHOXYSILANE |
| 16 | 3-THIOCYANATOPROPYLTRIETHOXYSILANE |

-continued

| Pixel number | Surface functionalization molecule |
|---|---|
| 17 | N-(3-TRIETHOXYSILYLPROPYL)-4,5-DIHYDROIMIDAZOLE |
| 18 | 2-(4-PYRIDYLETHYL)TRIETHOXYSILANE |
| 19 | N-(TRIETHOXYSILYLPROPYL)-ALPHA-POLY-ETHYLENE OXIDE URETHANE |
| 20 | TRIETHOXYSILYLPROPYLMALEAMIC ACID |
| 21 | (TRIETHOXYSILYL)PROPYLSUCCINICANHYDRIDE |
| 22 | N-(3-TRIETHOXYSILYLPROPYL)GLUCONAMIDE |
| 23 | BIS(2-HYDROXYETHYL)-3-AMINOPROPYL-TRIETHOXYSILANE |
| 24 | DIPHENYLDIETHOXYSILANE |
| 25 | TRIETHOXSILYLBUTYRALDEHYDE |
| 26 | 4'-AMINOBENZO-18-CROWN-6 |
| 27 | 5-AMINO-8-HYDROXYQUINOLINE DIHYDROCHLORIDE |
| 28 | 3-CHLOROPROPYLTRIETHOXYSILANE |
| 29 | 3-BROMOPROPYLTRIMETHOXYSILANE |
| 30 | 3-IODOPROPYLTRIMETHOXYSILANE |
| 31 | 3-MERCAPTOPROPYLTRIMETHOXYSILANE |
| 32 | 2-(DIPHENYLPHOSPHINO)ETHYL-TRIETHOXYSILANE |
| 33 | (2-TRIETHOXYSILYLPROPOXY)ETHOXYSULFOLANE |
| 34 | 3-(TRIHYDROXYSILYL)-1-PROPANESULFONIC ACID |
| 35 | 3-ISOCYANATOPROPYLTRIETHOXYSILANE |
| 36 | N-(TRIMETHOXYSILYLPROPYL)ETHYLENE DIAMINE TRIACETIC ACID, TRISODIUM SALT |

In some examples, the optical change pattern in response to an external stimulus (e.g., a solvent atmosphere) may be analyzed according to the example system of FIG. 7, as described above. In some examples, the optical change pattern generated by a liquid phase stimulus may be analyzed by immersion of the sensor into the stimulus (e.g., a test liquid sample) for a certain period of time (which may also be referred to as the incubation time). After the incubation, the sensor may be dried (e.g., by heating and/or by airflow). The dried sensor may then be analyzed for optical changes as described above.

In some examples, the photonic crystal combinatorial sensor may be reusable (e.g., where the external stimulus is removal from the sensor, such as a weakly interacting analyte such as long chain alkanes). For example, the photonic crystal sensor may be cycled between adsorption and desorption of a test sample multiple times with relatively little or no degradation of the sensor. Desorption may be facilitated by exposing the sensor to a neutral atmospheres, by introducing heat, or other suitable methods. This reversibility or recyclability of the sensor may be verified by comparing (e.g., subtracting) images of the sensor obtained before and after reversal (e.g., removal of adsorbed test samples) of the sensor.

In some examples, the photonic crystal combinatorial sensor may be only partially reversible or non-reversible (or non-reusable). For example, this may be useful where the sensor is intended to be a disposable and/or single-use device, or where reusing of the device is undesirable (e.g., for security and/or reliability reasons). It may be useful for a non-reusable device to be relatively low cost and/or amenable to large volume production.

In some examples, the photonic crystal sensor may be sensitive enough to produce a detectable response to an analyte present in a test sample at a relatively low concentration (e.g., on the order of several ppm).

In some examples, the time required for the photonic crystal sensor to exhibit a detectable response to an external stimulus may be dependent on the stimulus. For example, where the sensor is used for detection of an analyte, the strength (e.g., binding affinity) of the analyte-sensor interactions may affect how quickly a response is exhibited, with stronger interactions giving rise to quicker responses. The time required for the photonic crystal sensor to exhibit a detectable response may also be dependent on the concentration and/or strength of the external stimulus (e.g., concentration of an analyte in a test sample, volatility of an analyte, change in temperature, change in humidity, amount of test sample, etc.). For example, gas phase analytes with relatively high volatility (e.g., methanol), when presented in a test sample, may cause the sensor to exhibit a detectable response in a relatively short amount of time (e.g., several seconds) whereas solution phase analytes in a low concentration in the test sample may cause the sensor to exhibit a detectable response in a relatively long amount of time (e.g., several hours).

The photonic crystal materials may also have surface functionalization using other functional groups including, for example, silanes (e.g., with or without ionic, organic and/or inorganic groups attached), other organic functional groups, inorganic functional groups (e.g., having different types of interactions to test species), etc. Such functional groups may be bonded to the surface of the photonic crystal materials using suitable surface coupling reactions including, for example, silanization, imine bond formation, etc.

Although the above examples describe photonic crystal combinatorial sensors in which the photonic crystal materials in the array have different responses to external stimuli due to different surface functionalization, other methods of differentiating the responses of the photonic crystal materials may also be used. For example, the photonic crystal sensor may include one or more photonic crystal materials composed of different constituents, having different structure (e.g., different degrees of porosity, different layer thicknesses, different number of layers, etc.), being impregnated with different additives (e.g., quantum dots, fluorescent species, biological markers, dyes, polymers, etc.), different surface functionalization, and combinations thereof.

In some examples, in addition to or in place of sensor response due to changes in the effective refractive index of the photonic crystal material (e.g., increase or decrease of effective refractive index due to infiltration or removal of compounds, such as analytes and/or layer constituents, from the photonic crystal material), sensor response may also be due to changes in the structure of the photonic crystal material including, for example, changes in the porosity and/or thickness of one or more layers (e.g., due to infiltration or removal, such as by etching or dissolution, of compounds, such as analytes and/or layer constituents)

In some examples, the photonic crystal combinatorial sensor may be configured to detect any suitable analyte (e.g., any analyte whose adsorption or absorption would lead to a change in the effective refractive index and/or physical structure (e.g., porosity and/or thickness) of one or more layers of the photonic crystal material) including, for example, organics (e.g., alkanes, alcohols, amines, amides, imides, aromatic compounds, heterocycles, carboxylic acids, organic polymers, ethers, esters, etc.), inorganics (e.g., transition metal ions, metal ions, semimetals, alkaline and alkaline earth cations, group IV, V, VI, VII and VIII anions, inorganic polymers, etc.) and biomolecules (e.g., glucose and related carbohydrates, glucogen, enzymes and proteins, DNA, RNA, etc.), among others.

Although the photonic crystal material has been described as a one-dimensional photonic crystal material (e.g., Bragg stack), the photonic crystal sensor may also include one or more photonic crystal materials having other structures, including two- or three-dimensional structures (e.g., opal structure or 2D photonic crystals), single layered films and diffraction gratings, among others.

Example 1

An example study of the use of an example photonic crystal sensor is now described. In this example study, the photonic crystal sensor may be used for analysis of a series of alcohols and/or alkanes. In this example, unique color patterns may be obtained for each test vapor phase species. Three sets of measurements may preferably be conducted for each sample in order to verify the reproducibility of measurements using the example sensor and measurement system.

In this example, the sensor may have an array of 9 different photonic crystal materials having different responses to different alcohols and/or alkanes (e.g., using surface functionalization described with respect to FIGS. 3 and 4). In this example, the sensor may be exposed to each test species and the resulting response imaged and analyzed using the example system of FIG. 7. In this example, analysis of the sensor's response may be performed using principal component analysis.

Figure 8:
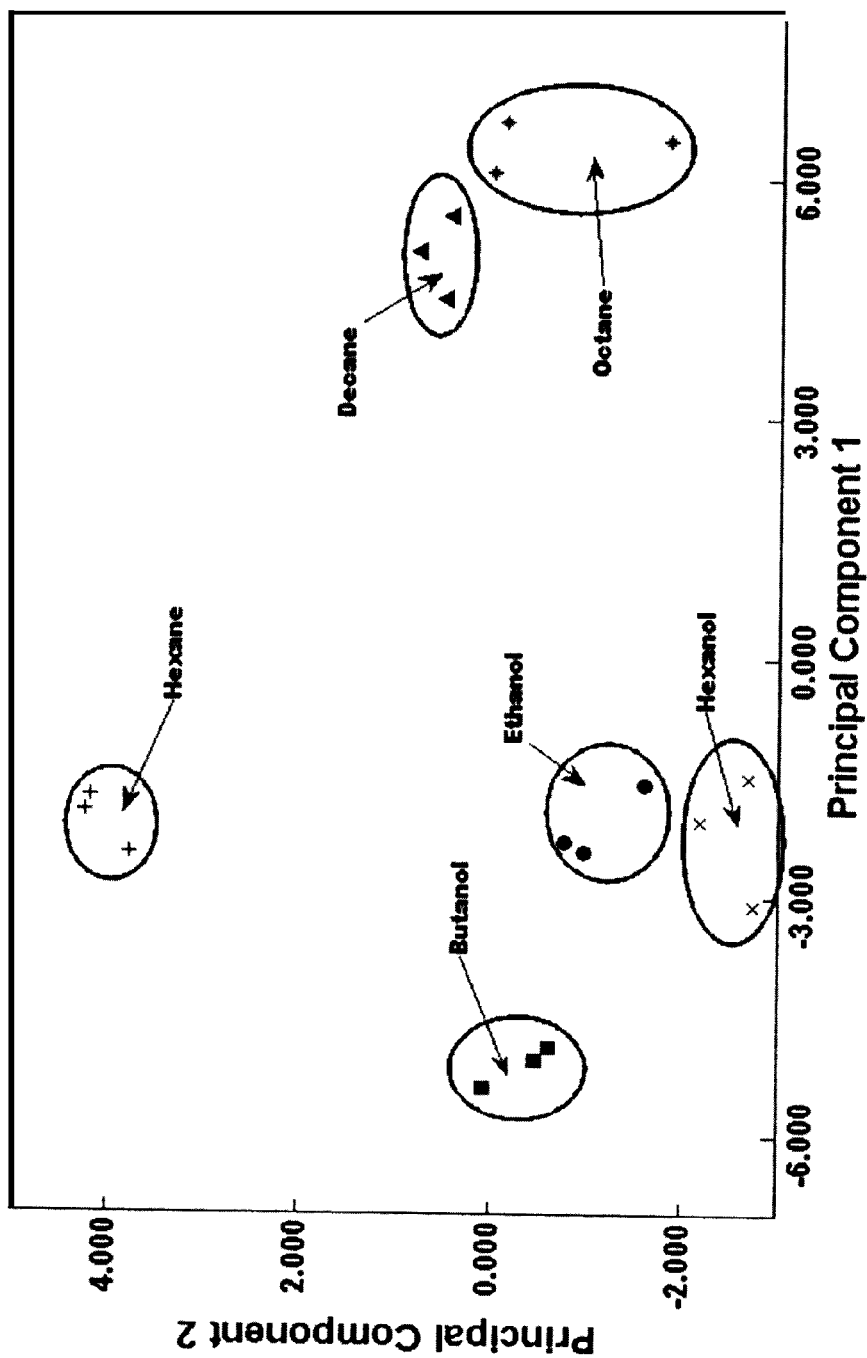
FIG. 8 shows an example principal component analysis for an example analyte, detected using an example photonic crystal combinatorial sensor.

FIG. 8 shows an example two-dimensional principal component analysis (PCA) based on color response of the example photonic crystal sensor when exposed to each test species. The analysis may be carried out using red, green and blue color levels. In this example, measurements for each test species were taken three times. In this example study, it was found that the first two principal components may account for about 82.22% of the variance in the measurements. This multivariate analysis method, which may be suitable for combinatorial platforms in general, may project a n-dimensional set of data (e.g., 27 dimensions in this example) into a new two- or three-dimensional set of coordinates (i.e., the principal components). Other methods for analysis of combinatorial sensor data may also be used.

Using PCA, clustering of data points may allow the assessment of the capabilities of discrimination of the sensor and/or may also demonstrate reproducibility of the measurements, for example as may be verified from the clustering of the data points for each test solvent. In this example, using only 9 different photonic crystal materials on the sensor (each having different surface functionalization), it may be possible to discriminate between different alcohols and/or alkanes. In this example, all the data points for the tested alcohols were found to group together in the negative range of the PCA plot, relatively separated from the data points for the tested alkanes.

Example 2

Another example study of the use of an example photonic crystal sensor is now described. In this example, an example of the photonic crystal sensor (the same as the example sensor studied in Example 1 above) may be used for diagnostic of a disease. In this example, test samples included four strains of bacteria, which may be commonly involved in cases of opportunistic hospital infections: *Escherichia Coli* (which may have been frequently associated with endogenous urinary tract infections), *Staphylococcus Aureus, Staphylococcus Epidermidis* and *Pseudomonas Aeruginosa*. In this example study, these bacteria were cultivated in about 5% sheep blood agar for about 24 h. Each of these species may produce a unique composition of volatile species as may be evidenced by their distinct and/or characteristic odour. Although the volatiles produced by the bacteria may be present in relatively small amounts, compared to compounds already existent in the agar plate itself, the culture headspace may be relatively saturated with the agar volatiles and/or the bacteria culture by-products, which may generate a distinct atmosphere composition.

In this example study, after growing a test bacteria for about 24 h, the Petri dish cover of the bacteria culture may be replaced with another Petri dish cover having the example photonic crystal sensor located on the inside, thus exposing the photonic crystal sensor to the test atmosphere produced by the test bacteria. An initial image of the sensor (i.e., at time t=0) may be obtained as a reference and subsequent images may be taken at regular time intervals. As the volatiles concentrate in the bacteria headspace, the photonic crystal sensor may develop a detectable response pattern, that may be imaged for analysis (e.g., PCA analysis).

In this example, the response of the sensor may preferably be fully reversed by exposing the sensor to a neutral environment (e.g., ambient atmosphere at about 50° C. overnight), allowing any test vapours to dissipate from the sensor. In this example study, the same sensor may be used in all analyses and measurements for each test species may be conducted for a set of three different plates of each bacteria strain. Analysis of the imaged response patterns may be carried out using PCA, as described above.

Figure 9:
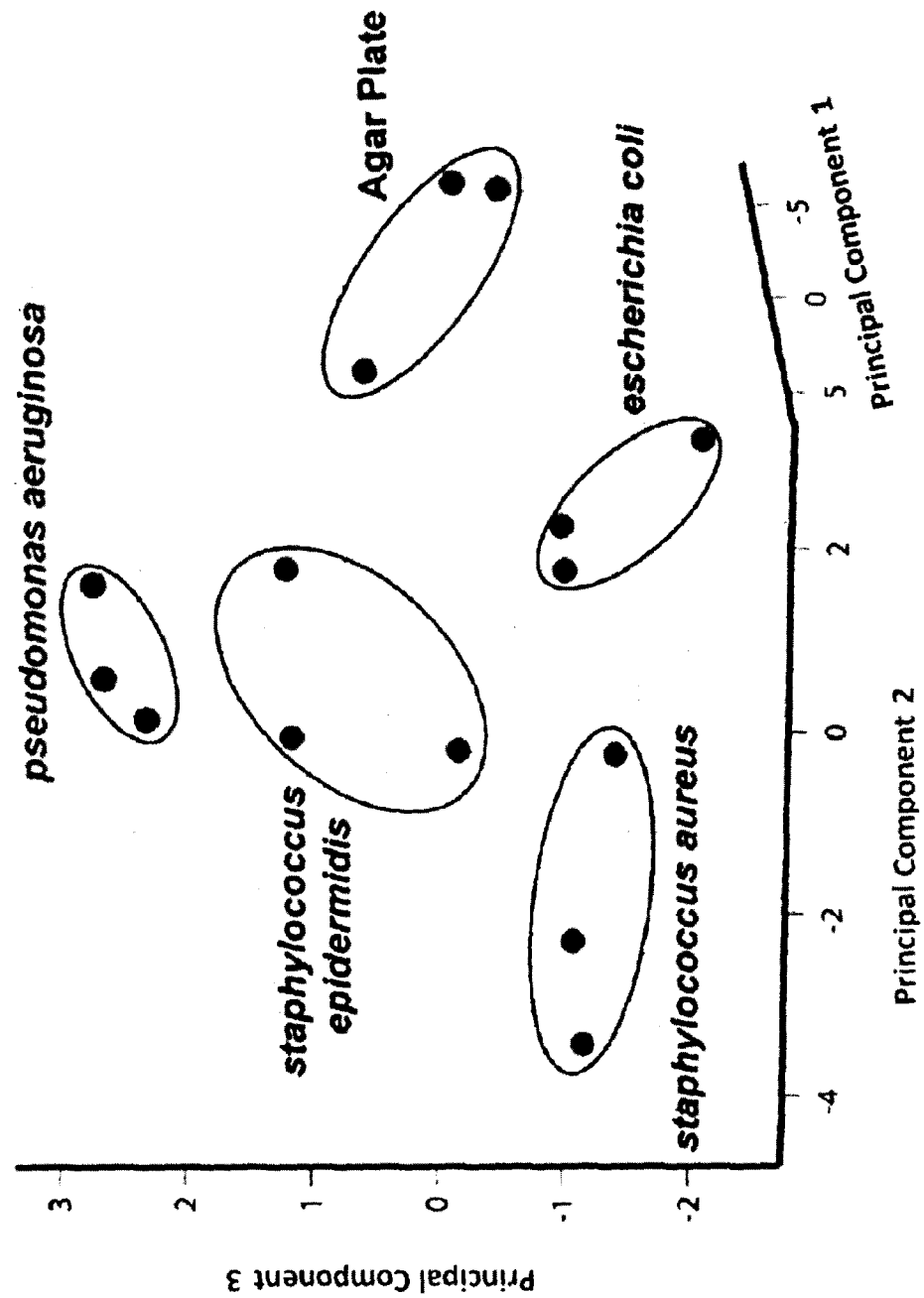
FIG. 9 shows an example principal component analysis for another example analyte, detected using an example photonic crystal combinatorial sensor.

FIG. 9 show an example three-dimensional PCA plot obtained from the example photonic crystal sensor, for different test species of bacteria, based on color response of the sensor when exposed to each test species. The analysis may be carried out using red, green and blue color levels. In this example, the first three principal components were found to account for about 94.34% of the variance of the measurements.

In this example, the example photonic crystal sensor was found to be suitable for distinguishing the test bacteria species analyzed, which in this example was observed to exhibit measurements distinct from the cluster containing non-cultivated blood agar plate points. This suggests that the photonic crystal sensor may be suitable for use in a relatively rapid and/or effective clinical alternative for quick bacteria identification in a relatively simple, reusable and/or low cost platform, and may be done without the requirement of complex and/or expensive sampling and/or analysis methods.

In some examples, the range of discrimination of test species may be increased by use of distinct surface functionalities, for example each having different analyte binding strengths and/or by use of a larger number of different photonic crystal materials in the sensor array.

Example 3

Another example study of the use of an example photonic crystal sensor is now described. In this example study, an example of the photonic crystal sensor may be used for analysis of solution phase analytes. Specifically, in this example, the example photonic crystal sensor was used for analysis of lead ions in water, which may be useful for the detection of contaminants in drinking water. In this example, lead(II) ions were selected as a target analyte due to its relevance in a number of environmental problems as a contaminant.

In this example, the example photonic crystal sensor may be configured similar to that illustrated in FIG. 10 (e.g., having the surface functionalization described with respect to FIG. 10). The example sensor may be immersed in a test solution containing lead(II) ions at a known concentration. After a pre-specified incubation time, the sensor may be removed from the test solution, dried and the response pattern developed by the sensor may be analyzed (e.g., using the example system of FIG. 7) using conventional methods, such as PCA. In this example, test solutions containing lead(II) ions at 10 ppm and 50 ppm concentrations were tested. Incubation times were 40 hours for the 50 ppm test solution and 5 hours for the 10 ppm test solution.

Figure 11:
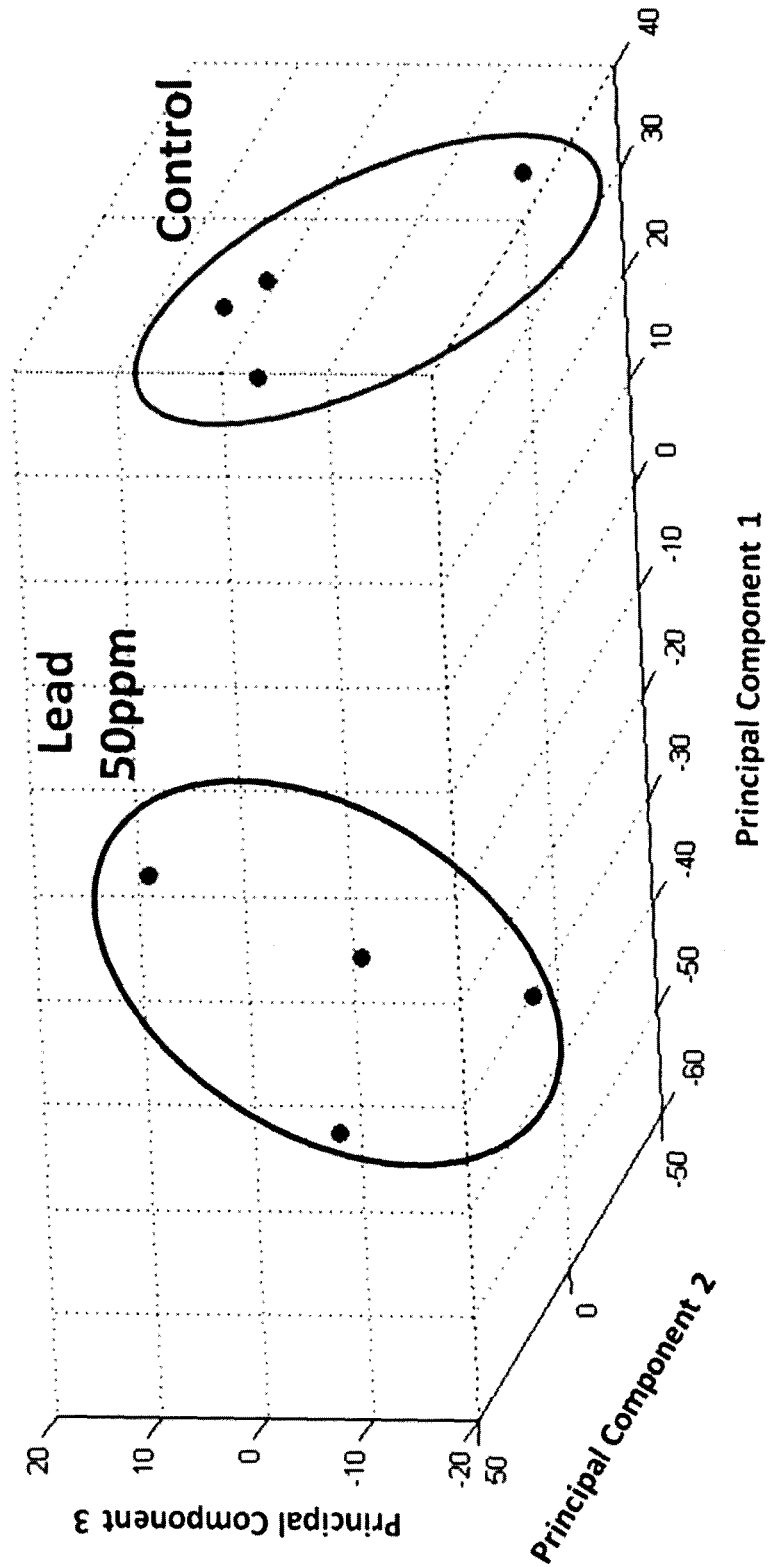
FIG. 11 and FIG. 12 show principal component analysis score plots for a 50 ppm and 10 ppm solution, respectively, generated using an example photonic crystal sensor.
Figure 12:
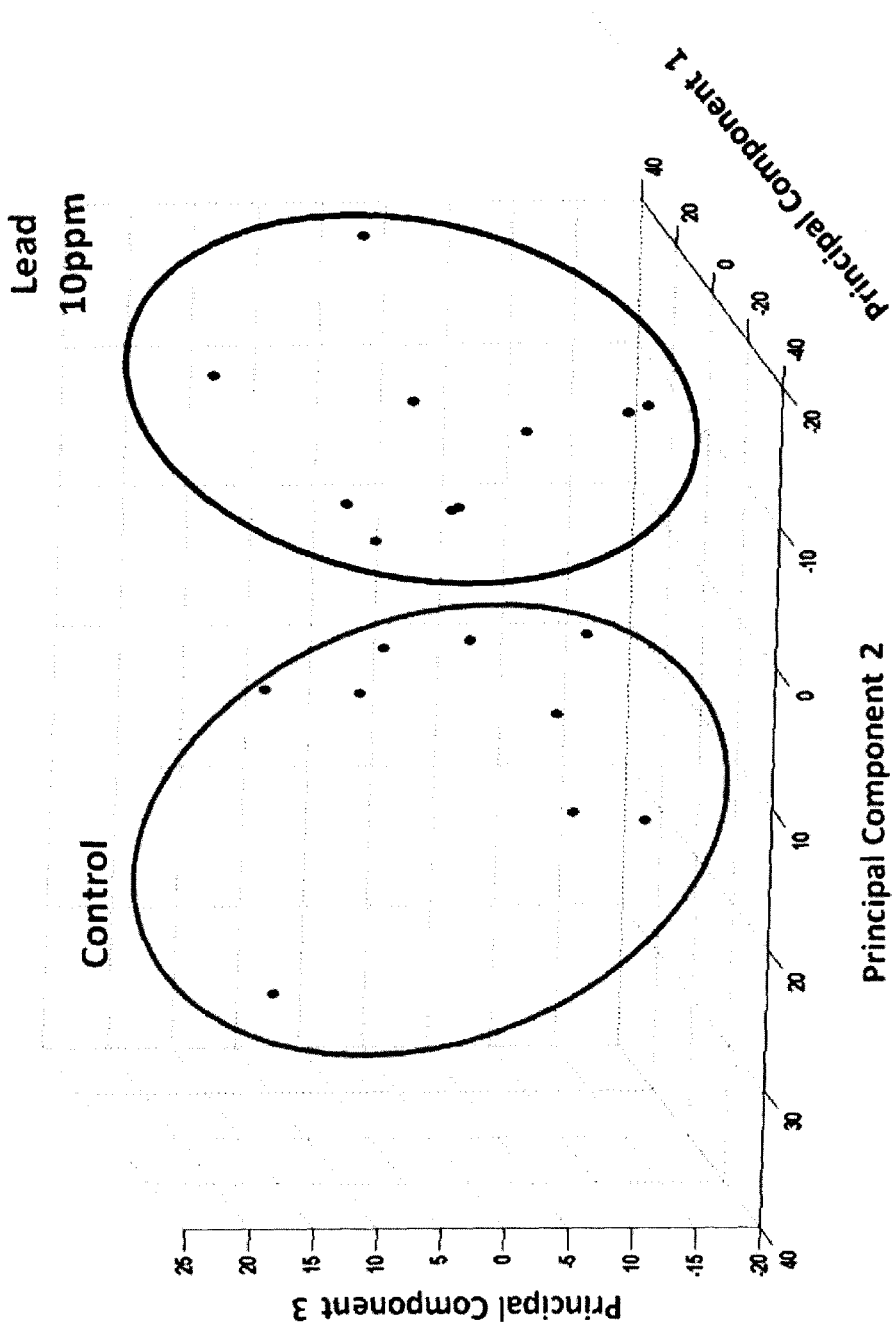

FIG. 11 and FIG. 12 show example PCA score plots for a 50 ppm and 10 ppm solution of lead(II) ions, respectively. In this example, the control sample may be deionized water.

Applications

In some examples, the present disclosure may provide a relatively effective and/or inexpensive optical (e.g., color) combinatorial sensor using photonic crystal materials. For example, the photonic crystal sensor may produce differentiable optical response patterns (which may be also referred to as "signatures" or "fingerprints") for structurally and/or chemically similar analytes.

An example photonic crystal combinatorial sensor may also be useful for relatively convenient identification of different classes and/or types of molecular species and/or bacteria (e.g., using PCA of digital images).

In some examples, the photonic crystal sensor may be useful for the development of combinatorial optical (e.g., color) sensing, and may be relatively simple and/or versatile to use and/or manufacture. For example, the photonic crystal sensor may be relatively simple and/or versatile to manufacture using conventional coating techniques, using the relatively wide variety of suitable nanoparticulate dielectric constituents, and/or by the relatively wide variety of suitable surface functionalization groups. Other methods of differentiating the response of the photonic crystal materials in an array (e.g., different structures, different constituents, different additives, etc.) may also add to the versatility of the photonic crystal sensor.

In some examples, the photonic crystal sensor may be useful in the areas of environmental monitoring (e.g., monitoring of pollutants in air and/or water), biomedical detection (e.g., detection of bacterial infections, diagnosis of lung cancer, tuberculosis, etc.), security (e.g., breathalysers, detection of dangerous compounds such as explosives and chemical warfare agents), food and beverage (e.g., detection of foodborne bacteria or spoilage, beverage quality and precedence, counterfeit detection), cosmetics and fragrances (e.g., characterization and/or quality control of perfumes), process monitoring, and automotive and aerospace, among others.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

The invention claimed is:

1. A photonic crystal combinatorial sensor comprising:
an array of photonic crystal materials, wherein, for each photonic crystal material of the array, a periodic difference in refractive indices within the photonic crystal material gives rise to a reflected wavelength in a respective initial wavelength range for that photonic crystal material;
the array of photonic crystal materials including at least:
a first photonic crystal material configured to have an internal structural response to an external stimulus, the internal structural response resulting in a change in the reflected wavelength of the first photonic crystal material, and
a second photonic crystal material configured to have a different response to the external stimulus than the internal structural response of the first photonic crystal material;
wherein the difference between the internal structural response of the first photonic crystal and the different response of the second photonic crystal material provides an optically detectable response pattern of reflected wavelengths in the array.

2. The photonic crystal combinatorial sensor of claim 1 wherein the periodic difference in refractive indices of at least one of the photonic crystal materials arises from a periodic difference in constituents of the photonic crystal material, the constituents having different refractive indices.

3. The photonic crystal combinatorial sensor of claim 1 wherein the periodic difference in refractive indices of at least one of the photonic crystal materials arises from a periodic difference in structure of the photonic crystal material.

4. The photonic crystal combinatorial sensor of claim 3 wherein the periodic difference in structure is a periodic difference in porosity within the at least one photonic crystal material.

5. The photonic crystal combinatorial sensor of claim 1 wherein at least one of the photonic crystal materials comprises alternating layers having a one-dimensional periodic difference in refractive indices.

6. The photonic crystal combinatorial sensor of claim 1 wherein at least one of the photonic crystal materials has a two-dimensional periodic difference in refractive indices.

7. The photonic crystal combinatorial sensor of claim 1 wherein at least one of the photonic crystal materials has a three-dimensional periodic difference in refractive indices.

8. The photonic crystal combinatorial sensor of claim 1 wherein the array comprises a pixelated arrangement of the different photonic crystal materials.

9. The photonic crystal combinatorial sensor of claim 1 wherein the internal structural response of the first photonic crystal material is a change in an effective refractive index of the first photonic crystal material.

10. The photonic crystal combinatorial sensor of claim 1 wherein the optically detectable response pattern is detectable in a visible wavelength range.

11. The photonic crystal combinatorial sensor of claim 1 wherein at least one of the photonic crystal materials has a surface functional group.

12. The photonic crystal combinatorial sensor of claim 1 wherein the difference between the internal structural response of the first photonic crystal and the different response of the second photonic crystal material is due to at least one of the group consisting of: a difference in surface functionalization, a difference in structure and a difference in materials.

13. The photonic crystal combinatorial sensor of claim 12 wherein the difference in surface functionalization is due to a difference in at least one of the group consisting of: attachment of at least one chemical group modifying surface chemical functionality, hydrophobicity, Coulombic interactions, Van der Walls interactions, hydrogen bonding ability, Lewis and Bronsted-Lowry acid-base interactions, charge transfer complexes, dipole-dipole interactions, magnetism, and nanostrucural features.

14. The photonic crystal combinatorial sensor of claim 1 wherein the external stimulus includes an analyte.

15. The photonic crystal combinatorial sensor of claim 14 wherein the analyte is in a gas or liquid phase, and the internal structural response of the first photonic crystal material is due to infiltration of the analyte into the first photonic crystal material.

16. The photonic crystal combinatorial sensor of claim 1 wherein at least one of the photonic crystal materials comprises nanoparticles.

17. The photonic crystal combinatorial sensor of claim 1 wherein the sensor is reversible back to the initial wavelength range for each photonic crystal material.

18. A method for optically detecting an analyte using a photonic crystal sensor, the method comprising:
   providing a photonic crystal combinatorial sensor comprising:
      an array of photonic crystal materials having an initial pattern of reflected wavelengths, wherein, for each photonic crystal material of the array, a periodic difference in refractive indices within the photonic crystal material gives rise to a reflected wavelength in a respective initial wavelength range for that photonic crystal material;
      the array of photonic crystal materials including at least:
         a first photonic crystal material configured to have an internal structural response to an external stimulus, the internal structural response resulting in a change in the reflected wavelength of the first photonic crystal material; and
         a second photonic crystal material configured to have a different response to the external stimulus than the internal structural response of the first photonic crystal material,
      wherein the difference between the internal structural response of the first photonic crystal and the different response of the second photonic crystal material provides an optically detectable response pattern of reflected wavelengths in the array,
   exposing at least a portion of the array of photonic crystal materials to a test sample;
      optically detecting a change in the array from the initial pattern of reflected wavelengths to the response pattern of reflected wavelengths, the response pattern being indicative of the analyte in the test sample; and
      determining presence of the analyte based on analysis of the detected change.

19. The method of claim 18 wherein optically detecting the change is based on detecting a visible optical change.

20. The method of claim 18 wherein optically detecting the change comprises calculating a difference between an image of the initial pattern and an image of the second pattern.

21. The method of claim 18 wherein determining the presence of the analyte comprises performing statistical analysis on the detected change.

22. The method of claim 18 further comprising reversing the sensor back to the initial pattern.

23. A use of the photonic crystal combinatorial sensor of claim 1 for detection of at least one of the group consisting of a pollutant, a bacterial, a disease marker, a target chemical, a biological agent, a level of humidity, and a level of concentration of an analyte.

24. The photonic crystal combinatorial sensor of claim 1 wherein the internal structural response is a change in a dimension of the first photonic crystal material.

25. The photonic crystal combinatorial sensor of claim 1 wherein the internal structural response is a change in a porosity of the first photonic crystal material.

26. The photonic crystal combinatorial sensor of claim 1 wherein the internal structural response is an infiltration of one or more pores of the first photonic crystal material.

27. The photonic crystal combinatorial sensor of claim 1 wherein the internal structural response is a removal of at least one compound from the first photonic crystal material.

* * * * *